United States Patent [19]

Hare et al.

[11] Patent Number: 5,177,120

[45] Date of Patent: Jan. 5, 1993

[54] CHAIN EXTENDED URETHANE DIACRYLATE AND DENTAL IMPRESSION FORMATION

[75] Inventors: Pamela H. Hare, Georgetown; Paul D. Hammesfahr, Dover, both of Del.

[73] Assignee: Dentsply Research & Development Corp., Milford, Del.

[21] Appl. No.: 120,269

[22] Filed: Nov. 13, 1987

Related U.S. Application Data

[63] Continuation-in-part of Ser. No. 935,455, Nov. 26, 1986, Pat. No. 4,813,875, which is a continuation-in-part of Ser. No. 636,136, Jul. 31, 1984, abandoned.

[51] Int. Cl.$^5$ .................... A61K 6/10; A61C 9/00; C08F 265/06
[52] U.S. Cl. .................... 523/109; 433/214; 525/293; 525/455; 525/920
[58] Field of Search .................... 433/214; 523/109; 525/920, 293, 455

[56] References Cited

U.S. PATENT DOCUMENTS

| | | |
|---|---|---|
| 3,453,242 | 7/1969 | Schmitt .................... 260/77.5 |
| 3,523,101 | 8/1970 | Reuter . |
| 3,878,036 | 4/1975 | Chang . |
| 3,907,751 | 11/1975 | Knight et al. . |
| 3,928,299 | 12/1975 | Rosenkranz et al. .......... 260/89.5 N |
| 3,950,300 | 4/1976 | Hittmair et al. . |
| 4,097,439 | 6/1978 | Darling . |
| 4,131,602 | 12/1978 | Hadakowski et al. . |
| 4,174,307 | 11/1979 | Rowe . |
| 4,182,829 | 1/1980 | Walkowiak et al. . |
| 4,233,425 | 11/1980 | Tefertiller et al. .................... 525/455 |
| 4,243,578 | 1/1981 | O'Sullivan et al. . |
| 4,258,164 | 3/1981 | Berlin et al. . |
| 4,320,221 | 3/1982 | Hoffman .................... 528/69 |
| 4,374,969 | 2/1983 | Frisch . |
| 4,383,091 | 5/1983 | Burton . |
| 4,404,296 | 9/1983 | Schapel . |
| 4,424,333 | 1/1984 | O'Connor . |
| 4,451,627 | 5/1984 | Frisch et al. . |
| 4,483,759 | 11/1984 | Szycher et al. . |
| 4,543,063 | 9/1985 | Cohen .................... 433/175 |
| 4,761,136 | 8/1988 | Madhavan .................... 433/214 |

FOREIGN PATENT DOCUMENTS

| | | |
|---|---|---|
| 0103420 | 3/1984 | European Pat. Off. . |
| 0167199 | 1/1986 | European Pat. Off. . |
| 0173085 | 3/1986 | European Pat. Off. . |
| 01772289 | 4/1986 | European Pat. Off. . |
| 0122611 | 10/1989 | European Pat. Off. . |
| 2388855 | 11/1978 | France . |
| 2391705 | 12/1978 | France . |

OTHER PUBLICATIONS

Technical Paper on Isocyanatoethyl Methacrylate: A Latent Crosslinker for Coating and Adhesive Resins by Paul E. Cranley.
Promotional Brochure on Developmental Monomer XAS-10743.00 Isocyantoethyl Methacrylate of Dow Chemical USA.
Product Data Bulletin No. 505 Revised Jan. 1966, *Poly B-D Liquid Resins.*
Standard Test Method for Rubber Property—Durometer Hardness.
Kenrich Petrochemicals, Inc., Now Deagglomerate, Couple and Catalyze Simultaneously.
Kenrich Petrochemicals, Inc., Ken-React Titanate Coupling Agent LICA 09.

*Primary Examiner*—Paul R. Michl
*Assistant Examiner*—Peter Szekely
*Attorney, Agent, or Firm*—Dale R. Lovercheck; Edward J. Hanson, Jr.; David E. Wheeler

[57] ABSTRACT

Disclosed is a new urethane polyacrylate having at least one terminal isocyanato acrylic pendent radical. Preferably the molecular chain within the acrylate caps has been extended with a polyhydroxy compound just before final end capping with isocyanato acrylic. The isocyanato acrylic is preferably isocyanato ethyl methacrylate and the urethane is diisocyanate capped polyether and the polyether radical is oxyalkylene. The method for producing the urethane polyacrylate involves end capping a polyol with diisocyanate yielding a reaction product with two reactive equivalents of isocyanate and then capping less than all of the isocyanate with a hydroxyacrylate, after which the remaining isocyanate is reacted with polyol to provide chain extension. The chain extending polyol is then capped with a isocyanato acrylic. Also disclosed is a new impression material for application to mammalian tissue and curing in contact therewith; the impression material including a free radical polymerizable resin, alkyl benzensulfonyl titanate, polymerization initiator, and filler; and a method of use.

22 Claims, No Drawings

CHAIN EXTENDED URETHANE DIACRYLATE AND DENTAL IMPRESSION FORMATION

BACKGROUND OF THE INVENTION

This is a continuation-in-part of U.S. patent application Ser. No. 935,455, filed Nov. 26, 1986 now U.S. Pat. No. 4,813,875, which is a continuation-in-part of U.S. patent Ser. No. 636,136, filed Jul. 31, 1984, now abandoned.

This invention relates to a new composition of matter that is a urethane diacrylate which is especially useful as a compound for use in compositions for forming impressions of mammalian tissue especially in dental applications—compositions that accurately conform to dental surfaces to be recorded, and to a method of producing the urethane diacrylate. The invention also relates to such new impression materials that are free radical polymerizable resins and contain alkyl benzensulfonyl titanate, polymerization initiator and filler.

Methods of forming dental impressions are well known, as are dental impression materials that are capable of accurately reproducing the surface contours and dimensions of oral tissues required in preparing dental prostheses. Since anatomic structures and preparations for prosthetic appliances are usually undercut, preferred impression materials are elastic or rubbery, ranging from gels, such as agar or algin preparations, to elastomers, such as rubbers, silicones, and polyethers. The nonaqueous elastomers are preferred because of their extreme dimensional accuracy and their relative stability under ambient conditions. In spite of all the improvements which have characterized current dental impression materials, they are still greatly limited by clinical factors when they are used in vivo.

It is known to prepare elastomeric impression materials by taking two separate pastes (one containing catalyst and the other containing an accelerator), placing measured amounts of each on a pad of parchment or polyethylene-coated paper and immediately mixing them with a spatula into a substantially homogeneous mass. Such impression materials must be used immediately after mixing; and while curing to set is rapid, it must be timed to allow placement by fast and slow dental practitioners and because the curing time is built in, special problems cannot be controlled with any degree of accuracy by the dental practitioner. Also, the act of mixing tends to introduce air bubbles into the viscous pastes and these bubbles are difficult to eliminate, tending to cause surface imperfections in the finished impression or distortion of the impression. Mixing is inconvenient and a source of inconsistency.

In the usual practice, a dental practitioner places the mixed paste in juxtaposition to the dental tissues, using either a supporting tray to contain the paste or a combination of a placement syringe and a supporting tray. The dental practitioner or dentist and the patient then wait, sometimes for ten minutes, for the polymerization reaction to progress to completion and the material to become sufficiently elastic so that the impression may be removed from the tissue without distortion of the remembered shape or form. The rate of faulty impressions is quite high due to the patient's natural tendency to move during this time and a gagging reflex is common. The dental practitioner loses valuable time while he is thus inactivated, plus time needed for the often required retakes.

Materials commonly used for taking impressions are polysiloxanes such as described in U.S. Pat. No. 3,950,300, polyethers such as described in U.S. Pat. No. 3,453,242, and other elastomeric materials having properties more fully described in American Dental Association Specification 19.

SUMMARY OF THE INVENTION

The new urethane polyacrylate having at least one isocyanato acrylic pendent group provides an excellent dental composition component that, in preferred forms, is non-toxic in use in the oral cavity and will assume a permanent elastomeric memory when cured. When the new urethane polyacrylate is provided with an initiator activated by actinic light within the visible light range of about 360 to about 600 nanometers it can be substantially stable against assuming a permanent remembered form when stored actinic light free, and then on exposure to light filtered to limited wavelengths within the visible light range for one (1) minute cure to a depth of one (1) inch.

The preferred compound is a chain extended urethane polyacrylate made according to the following preferred method. First, a polyhydroxy compound is reacted with a polyisocyanate forming a first reaction product having about 2 equivalents of reactive isocyanate. This first reaction product is then reacted with less than two equivalents of a compound having an acrylic pendent radical and another reactive site preferentially reacting with the first reaction product, forming a second reaction product. The second reaction product is then reacted with a polyhydroxy compound to form a third reaction product. This third reaction product is then reacted with an isocyanato acrylate compound to form the urethane polyacrylate of the present invention.

By another aspect of the invention a new impression material for application to mammalian tissue and curing in contact therewith to set the impression is provided. The impression material includes a free radical polymerizable resin, alkyl benzensulfonyl titanate, polymerization initiator and filler. Also provided is a method for using the new impression material.

DESCRIPTION OF THE PREFERRED EMBODIMENT

The present invention in a preferred embodiment of one of its aspects is a new composition of matter in the form of a new compound having the following general formula:

wherein
$R_1$ is

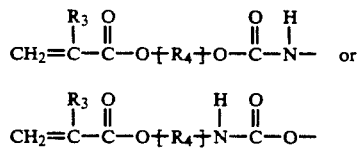

and $R_1$ may be the same or different and each independently preferably have from 5 to 100 C, more preferably 5 to 15 C and most preferably 6 to 11 C. $R_3$ is H, alkyl, sub alkyl, aryl, sub aryl, F, CN. (The term sub as used in this application means substituted, which means that at least one non C or H atom would be present or a radical such as a benzene ring would be present. By acrylic it is meant any pendent acrylic radical, by diacrylic it is meant a radical or a compound with two pendent acrylic radicals.)

$R_3$ may be the same or different in each position.

$R_3$ is preferably methyl.

$R_4$ is a divalent hydrocarbon radical or divalent sub hydrocarbon radical and may be straight or branched chain or cyclic or a combination thereof. By cyclic it is meant to include aromatic and heterocyclic compounds.

$R_4$ preferably has from 2 to 100 C, more preferably $R_4$ is an aliphatic radical having from 2 to 100 C, more preferably 2 to 10 C and most preferably 2 to 6 C.

[A] is any polyurethane, polyester or polyether oligomer. (By poly as used in this application it is meant two or more. By oligomer it is meant a molecular weight of between about 500 and 5000. The moleculer weight of the oligomer and its resulting physical characteristics can be controlled by carefully choosing the substitutents used to make up the oligomer in a manner that is well known to those skilled in the art. For example, [A] may be chosen to be a low molecular weight polyether when a relatively rigid polymer is desired, and [A] and other substituents may be chosen to have a high molecular weight when a relatively soft pliable polymer is desired. As will be recognized by those skilled in the art, the concentration and the type of fillers used in the polymer, and other factors will affect the properties of the polymer to some extent.

In general, however, when a relatively rigid polymer is desired the molecular weight of the oligomer should be in the range of about 500-2000 and preferably 650-1500. When a soft, pliable polymer is desired, the oligomer will have a molecular weight in the range of about 1500-5000, or higher, preferably about 2000-4000.

The soft, pliable resins have elastic properties and may be characterized generally as being capable of about 50% or more elongation from the unstressed state before rupture or tearing after being cured.

The rigid polymers may be characterized generally as being capable of about 50% or less elongation from its unstressed state, before tearing or rupture.

The elongation property described herein is a characteristic of the unfilled resin.

The term backbone as used in this application means the structure of the oligomer between the two urethane groups closest to the terminal ends of the molecule).

A presently preferred composition, which is an important aspect of the present invention, is where A is represented by [$R_5$] —X [—$R_6$].

X is a polyurethane and $R_5$—X and $R_6$—X are joined by a urethane or polyurethane linkage.

X may broadly contain any hydrocarbon or sub hydrocarbon radical and may be straight or branched chain or cyclic or a combination thereof and may also be one or more of the following radicals: siloxane, sub siloxane, sulfone, etc., but is preferably a polyether or a polyester or a mixture thereof, most preferably X is a polyether and the polyether radical is a straight chain.

$R_5$ and $R_6$ are each independently divalent hydrocarbon radicals or divalent sub hydrocarbon radicals and may be straight or branched chain or cyclic or a combination thereof and may also be siloxane or sub siloxane radicals.

By lower alkyl, it is meant alkyl or substituted (sub) alkyl of 1-25 carbons, preferably 1-15 carbons and more preferably 1-12 carbons. By alkylene is meant an alkyl group having 2 to 40 carbon atoms, preferably 2 to 30 carbon atoms and most preferably 2 to 15 carbon atoms, unless otherwise specifically defined.

Sub or substituent is not limited to but is meant to include, as representative examples, radicals selected from the group consisting of halogen, lower alkyl, oxy-lower-alkyl, silyl-lower-alkyl, phenyl, halo phenyl, alkoxyphenyl, trihalomethyl, dihalomethyl, and similar substituents where lower alkyl has 1 to 6 carbons.

$R_5$ and $R_6$ preferably have from 3 to 100 C, more preferably $R_5$ and $R_6$ are aliphatic radicals having from 2 to 100 C, more preferably 2 to 10 C. $R_5$ and $R_6$ may be the same or different.

The person skilled in the art would tailor the [A] radical to achieve such characteristics as he may choose. The particularly preferred [A] radical, especially with both $R_5$ and $R_6$ joined to X by a urethane linkage with X being of substantial molecular weight and both $R_5$ and $R_6$ of low molecular weight, is of special preferred merit, especially in the more preferred embodiments of the present invention.

In the preferred embodiment A is the radical

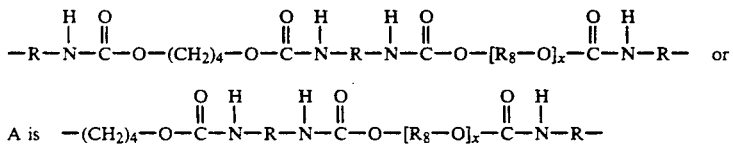

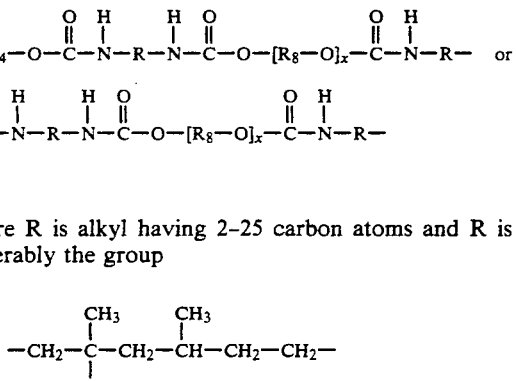

where R is alkyl having 2-25 carbon atoms and R is preferably the group $$-CH_2-\underset{\underset{CH_3}{|}}{\overset{\overset{CH_3}{|}}{C}}-CH_2-\overset{\overset{CH_3}{|}}{CH}-CH_2-CH_2-$$

and $R_8$ is alkyl of 2-25 carbon atoms and preferably is the group

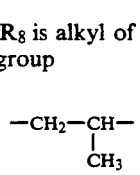

and x is 10 to 100.

In the preferred embodiment, the polymers of the present invention can be broadly described as comprising a molar ratio of polyol/polyisocyanate/hydroxyalkyl methacrylate/dihydroxy compound/isocyanatoacrylate of about 1:2:1-1.5:1-1.5:0.5-1.

In the preferred reaction:

$R_1$ is a radical preferably formed by reacting a hydroxy acrylate with an isocyanate group on a prepolymer polyurethane oligomer and is drawn to include the urethane group contributed by the isocyanate, or a radical contributed entirely by an isocyanato acrylate when the isocyanato acrylate is reacted with a hydroxy group on a prepolymer polyurethane oligomer.

In [$R_5$] X [$R_6$], $R_5$ would be the terminal radical in the prepolymer polyurethane oligomer when the terminal urethane group has been drawn as part of $R_1$. For clarity of explanation, in Example 1 this would be the trimethyl hexamethylene radical from trimethyl hexamethylene diisocyanate and would include the other urethane group contributed by the diisocyanate. $R_6$ would be the oxyalkylene residue of the 1,4 butane diol.

The more preferred compounds have the formula:

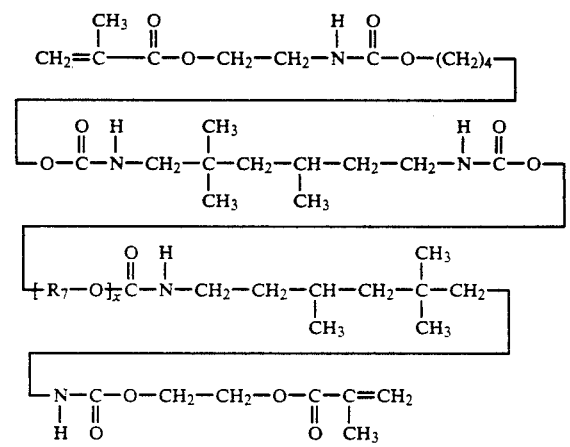

where $R_7$ is alkylene or sub alkylene and x is 10 to 100; or

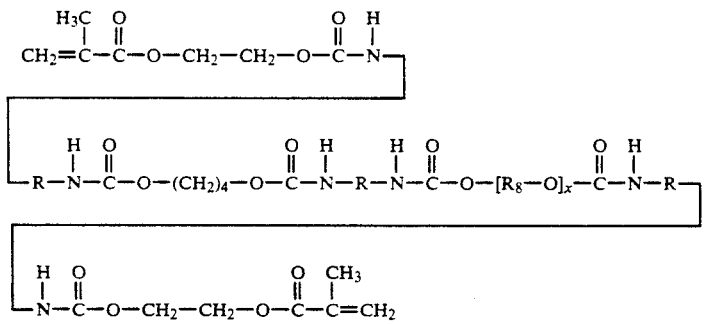

wherein
R is alkyl of 2 to 25, preferably 2 to 15 carbon atoms and
$R_8$ is alkyl of 2 to 25 and preferably 2 to 8 carbon atoms, and
x is 10 to 100.

The preferred method of preparing the new compound of the present invention, which method is an important aspect of the present invention, is to form a first reaction product by reacting a polyhydroxy compound with a polyisocyanate, then reacting the first reaction product with the acrylic of $R_1$ in an amount of at least approximately 1 equivalent and leaving at least approximately 1 equivalent of unreacted isocyanate, then this second reaction product is chain extended at the unreacted isocyanate with a polyhydroxy alkylene, sub alkylene, arylene, or sub arylene of $R_6$ and this third reaction product is then end capped at its chain extended sites with the isocyanatoacrylate of $R_1$. Preferably the isocyanate and hydroxy reaction compounds are di or tri isocyanate or di or tri hydroxy compounds, more preferably diisocyanate and dihydroxy compound. By equivalent as used in this application it is meant the theoretical reactive potential of the particular group in each molecule.

As a more general description of the method of preparing the preferred embodiments of the new chain extended urethane polyacrylate, first a polyhydroxy compound is reacted with a polyisocyanate forming a first reaction product having about 2 equivalents of reactive isocyanate. This first reaction product is then reacted with less than two equivalents of compound having an acrylic pendent radical and another reactive site preferentially reacting with said first reaction product, forming a second reaction product. Compound as used in the context of this patent application can be made up of compounds of different molecular structure having the recited characteristics or of a quantity of a single molecular structure. The use of the term equivalents (here as stated, less than 2 equivalents) as used in the context of this patent application refers to the reactive potential under the conditions of the recited reaction.

The second reaction product is then reacted with a compound chosen from the group consisting of polyhydroxy alkylene, sub alkylene, arylene, sub arylene, and oxyalkylene or sub oxyalkylene to form a third reaction product. This third reaction product is then reacted with an isocyanato acrylate.

The theoretical reaction forming the first reaction product is a capping of a portion of the reactive isocyanate to form polyurethanes having a radical bridging two urethane groups and leaving other reactive pendent isocyanate reaction sites in the first reaction product.

The first reaction product is then reacted with an acrylic compound leaving at least one pendent acrylic radical on at least a substantial portion of the reaction molecular yield of the second reaction product. Because less than the full stoichiometric amount of acrylic compound necessary to satisfy all of the pendent isocyanate is used, substantial pendent isocyanate reaction sites remain. The reacting of the pendent isocyanate reaction sites in the second reaction product with the polyhydroxy compound is understood as a chain extending reaction, at least predominantly capping the pendent reactive isocyanate. Preferably, the first polyhydroxy compound (the one used in forming X) is a dihydroxy oxyalkylene and the second polyhydroxy compound (the residue of which is $R_6$) is a dihydroxy alkylene and the isocyanato acrylic compound is isocyanato alkylene acrylate.

In another preferred embodiment, the compositions of the present invention are prepared, in general, by forming a first reaction product by reacting a polyhydroxy compound with a polyisocyanate to form a polyurethane. An excess of polyisocyanate is added to form an isocyanate terminated prepolymer. Part of the terminal isocyanate end groups are capped with the acrylic of $R_1$ and the remainder are chain extended with 1, 4 butanediol. A reaction product of polyisocyanate and an hydroxy acrylate is then reacted with the chain extended prepolymer.

More specifically, there is provided a method for making a compound having the formula:

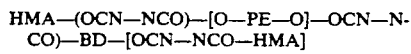

HMA—(OCN—NCO)—[O—PE—O]—OCN—N-CO)—BD—[OCN—NCO—HMA]

wherein O—PE—O represents hydroxy substituted polyether, polyurethane or polyester; OCN and NCO represent isocyanate groups and —(OCN—NCO)— represents polyisocyanate; HMA represents unsaturated hydroxy substituted organic acid ester, and BD represents lower alkyl diol.

The polymerization comprising sequentially the steps of:

(a) reacting about 1 equivalent of hydroxy substituted oligomer with about 2 equivalents of diisocyanate to form a polyurethane chain having 2 isocyanate end groups (b) reacting the polyurethane formed in step (a) with about ½ equivalent of an unsaturated hydroxy substituted organic acid ester to predominantly form a polyurethane having an isocyanate group on one end and an unsaturated organic acid ester at another end thereof (c) reacting the product of step (b) with a lower alkyl diol to react with said isocyanate group to form a polyurethane having an unsaturated organic acid ester at one end and a hydroxy at another end thereof (d) reacting the reaction product of an unsaturated organic acid ester with a diisocyanate with the polyurethane formed in step (c) to from a polyurethane having an unsaturated hydroxysubstituted organic acid ester on at least 2 ends thereof.

In the preferred method, PE is polyether, the polyisocyanate is trimethyl hexamethylene diisocyanate, HMA is hydroxyethylmethacrylate, and BD is butanediol.

As a general proposition suitable polyhydroxy compounds, polyisocyanate compounds and acrylate compounds for use in the present invention are taught by a wide variety of references, including U.S. Pat. No. 4,182,829, the contents of which are incorporated herein by reference. Suitable alkyleneisocyanatoacrylate compounds for use in the present invention are taught by U.S. Pat. No. 4,233,425 the contents of which are incorporated herein by reference.

The saturated di or tri polyhydroxy compounds which are especially useful in preparing the urethane reaction product X for the practice of the present invention may comprise any of a wide variety of materials especially polyether, polyesters and polycarbonate. Especially preferred are those having substantially no ethylenic unsaturation therein. Thus, one or more materials having two hydroxylic functionalities, which material is not ethylenically unsaturated may be so employed. Preferred materials include aliphatic diols having from about 8 to about 20 carbon atoms between the hydroxylic functions such as dodecene diol, decane diol, etc. Certain prepolymeric materials, such as the polyalkylene ether glycols are even more preferred: Accordingly, materials such as polymethylene ether glycol, polyethylene ether glycol, polypropylene ether glycol, polybutylene ether glycol, etc. may be so employed It will be understood by those skilled in the art that a wide variety of such ether glycols may be useful in the practice of the present invention. Preferred materials for use in accordance with the present invention are polybutylene ether gylcol (also called polytetramethylene ether glycol) and polypropylene ether glycol. As will be readily appreciated, the foregoing polyalkylene ether glycols are generally available as mixtures of species having differing molecular weights.

It will be appreciated that a wide variety of polyisocyanates may be employed in preparing the urethane reaction product of X in accordance with the present invention. Exemplary species include the hexamethylene diisocyanate, tetramethylhexamethylene diisocyanate, isophorone diisocyanates, trimer of isophorone diisocyanate and trimer of 1,6 hexamethylene diisocyanate along with many others. It has generally been found most preferred to employ diisocyanate species which are either aliphatic or cycloaliphatic in nature. While such non-aromatic polyisocyanates are preferred, aromatic materials such as toluene diisocyanate and methylene bisphenyl-4-diisocyanate may also be used. The isocyanate functions of the foregoing materials may be viewed as being separated by a number of carbon atoms. Such number of carbon atoms is preferably from about 6 to about 20. A preferred diisocyanate for use in accordance with the present invention is trimethyhexamethylene diisocyanate.

The glycol is reacted with one or more equivalents of polyisocyanate, preferably diisocyanate, material of this invention in such a fashion as to always have isocyanate functions in excess over glycol functions. The amount of isocyanate moieties to be reacted with the hydroxylic species of the glycol mixture is such that there will be a final stoichiometric excess of isocyanate over hydroxyl. It is preferred that this excess be from about 50% to about 150% on a molar basis with about 75% to 125% being preferred. It is still more preferred that about 100% molar excess of isocyanate be included in excess over the molar amount of hydroxylic functions. The isocyanate moieties are included in excess so as to provide reactive sites for the capping and chain extending of the urethane oligomers with polymerizable acrylic functions.

The acrylates of $R_1$ of the present invention may be chosen from a variety of compounds in accordance with the present invention. Preferred acrylates are hydroxyalkylation products of acrylic and/or methacrylic acid, such as acrylic acid hydroxyethyl ester, acrylic acid hydroxypropyl ester, methacrylic acid hydroxyethyl ester and methacrylic acid hydroxypropyl ester. The most preferred are the methacrylic acid hydroxyethyl esters.

The second reaction product, which is preferably basically a monoacrylated urethane, is chain extended with additional di or polyhydroxylic compounds or amines chosen from such glycols and amines as the ethylene, propylene, diethylene and butylene glycols. The most preferred chain extender is 1,4 butylene glycol.

The preferred alkyleneisocyanatoacrylate of $R_1$ may be chosen from a variety of compounds in accordance with the present invention. They are exemplified by such preferred compounds as isocyanatoalkylene meth-acrylates and the most preferred isocyanatoethylmethacrylate.

In accordance with this invention, the polymerizable oligomers or compounds formed hereby are preferably included in compositions that are dental impression materials for forming impressions of living mammalian tissue to set the impression thereof. The especially preferred compositions are dental impression materials.

The dental impression material composition of the present invention is preferably substantially stable against assuming a permanent remembered form when stored actinic light free. The composition is preferably stable when stored as a single one-component material for a long period of time actinic light free preferably being stable for at least one month, more preferably three months, and most preferably for six months or more. By one-component, it is meant that the dental impression material can be stored in the exact form that it will be used by the dentist so that he preferably does not need to do anything other than mold the composition to the surface (surfaces) that is to have its impression made.

The preferred embodiment providing a shelf-stable storable impression material is one having a photoinitiating system. The photoinitiating system may be one of many known in the art to promote polymerization of unsaturated acrylic groups when activated by actinic light of the appropriate wavelengths, strength and length of exposure time. Such systems include, but are not limited to camphoroquinone and other alpha-beta diketones, alone or with reducing agents, such as secondary and tertiary amines; compounds known to catalyze photopolymerization of acrylates upon irradiation by visible light. Materials such as benzoin and benzoin methyl ether which are known to be photopolymerization catalysts utilizing light in the UV portion of the electromagnetic spectrum are operable to cure the presently preferred polymers, but UV light is considered generally undesirable in most instances.

In the aspect of the present invention involving the actinic light activated photopolymerizing composition, the composition is for health and safety reasons preferably one that can be expeditiously cured using light filtered to limit the wave lengths to the visible light range of approximately 360–600 nanometers. More preferably the curing is carried out with the greater portion of the light being within the 400–500 nanometer range.

The amount of photopolymerization initiator or sensitizer and the types are selected with due consideration to the intensity of the light source and the activating wavelength(s) and their own capacity to initiate polymerization. Photoinitiators, for example, camphoroquinone, may be typically used in concentrations between 0.001 and 10% by weight of the polymerizable resin present, preferably between 0.01 and 5%. Accelerators for the photoinitiation for example, tertiary amines, including, for example, methyldiethanolamine, diethanolamine, triethanolamine, 4-ethydimethylaminobenzoate, or 4-dimethylaminobenzonitrile may be used. These are typically used in amounts of between 0.001 and 10% by weight of the polymerizable resin present, preferably between 0.01 and 5%.

Because the urethane polyacrylate (di or tri acrylate) prepolymer that is the preferred compound for use in the dental impression material composition of the present invention is also an independent aspect of the present invention it is pointed out that the urethane polyacrylate polymer can be applied to the preparation of a self-curing dental impression using the more conventional types of curing systems employed in dental impression materials, such as, a paste containing as the initiator, benzoyl peroxide, with fillers such as quartz, talc and silica, a diluent such as polypropylene glycol with a molecular weight, for example, of 4,000 and a stabilizer such as BHT (butylated hydroxy toluene). The base paste would correspondingly contain an accelerator such as dihydroxyethyparatoluidine, a diluent such as polydimethylsiloxane and fillers. By "self-curing" it is meant that a dental impression material, in the form in which it is used, will cure at a predetermined rate due to built-in curing activaters which need no external initiation, such as the actinic light initiation of the more preferred embodiments of the present invention. It is also within the purview of the present invention to provide a self-curing dental impression material with actinic light activated components and thereby obtain a dual cure system that when mixed will cure in the typical self-cure fashion or be accelerated in cure through the use of actinic light.

The impression material can be a viscous liquid, or it can be modified with fillers to result in more viscous pastes or even putties. Such fillers should have suitable optical characteristics in the more preferred embodiments so as not to interfere with the transmission of actinic light through the material in order to permit initiation of the photoinitiator system. The filler particles should have size and surface area appropriate to effect the desired viscosity change.

Generally the non reinforcing fillers are used primarily for viscosity modification. Extending fillers are those having a surface area less than 50 meters per square gram, and include calcium carbonate, fused quartz powder, powdered calcium silicaluminate, titanium dioxide, zirconium silicate, aluminum silicate, crystobalite, feldspar, etc. The preferred fillers are silicon dioxide such as fused quartz especially in visible light cured formulations. The fillers may be ground or formed by a variety of means to provide particulate powdered filler of preferred sizes between 0.001 and 100 microns, depending on the application. Particles of individual average sizes of 0.01 and 40 microns are especially preferred.

Reinforcing fillers may also be used in the composition of the present invention. Preferred reinforcing fillers have a surface area of at least 50 square meters per gram and are exemplified by pyrogenically-produced silicon dioxide, silicic acid hydrogels dehydrated so as to maintain their structure, silicon dioxide Aerogels, and precipitated silicon dioxide.

All of these fillers; but especially the reinforcing fillers, may have organosilyl groups on their surface by pretreating with, for example, dimethyl-halogen silanes; or for example, by reaction of aqueous silica sol with organo halogensilanes; or may be rendered hydrophobic in some other way. Mixtures of different fillers can be used. Non-reinforcing fillers may be used at concentrations of at least 20% by weight relative to all of the prepolymers present, whereas reinforcing fillers may be appropriately used in the compound at from 1% to 80% by weight, relative to the total weight of all prepolymers present. Preferred overall filler contents are from 5 to 95%, more preferably 20 to 90%, and most preferably, for some applications, 40 to 85% by weight based on the composition weight. In the case of actinic light-cured compositions, an important consideration is that the amount and the type of filler is so selected that actinic irradiation may pass through the polymerizable mass in order that polymerization can occur upon irradiation to the depth of the impression but the filler need not match the refractive index of the resins exactly.

Alkyl benzensulfonyl titanates combined with the free radical initiated polymerizable resin, polymerization initiator and the filler, form an important feature of one aspect of the present invention. The preferred alkyl benzensulfonyl titanate is neoalkoxy, tridodecylbenzenesulfonyl titanate (Titanium IV neoalkoxy, tris (dodecylbenzene) sulfonato). It is believed that the titanate gives a better homogeneity by improving the coupling of the filler and the resin. The titanates also are believed to have some accelerating effect in the free radical initiated polymerization of the polymerizable resin even in the low energy visible light initiation of the acrylic cross linking polymerization. The titanate is preferably present in an amount of 0.001 to 2% by weight of the total composition, more preferably 0.005 to 1% and most preferably 0.01 to 0.5%.

Other formulation auxiliaries may also be used. Organic resins, for example PVC powder or methacrylate polymer powder, polyethylene and the like, may be used as suitable extenders and plasticizers. The compositions of the invention may be stabilized by the addition of hydroquinone, catechol, and other similar well-known polymerization inhibitors for the polymerization of (meth) acrylate compounds. Other optional ingredients include pigments and flavoring substances. In one embodiment, for example, the heavy body material may include peppermint flavoring. Still other plasticizers may include, for example, siloxanes, silanes, phthalates, glycerides, and other materials known in the art. Such plasticizers are generally added to alter the hydrophobicity, the softness or hardness of the composition, its viscosity or tackiness, etc. Silane, for example, is a plasticizer which also acts as a binder for the resin and the filler particles.

The dental impression material or composition in the usual situation is preferably non-adhering to tooth enamel, amalgam, composite tooth fillings, metal bridgework, and other substances commonly found in a variety of different patients so that the composition can have relatively universal use. The composition should have the non-adhering ready release characteristic when or after it is changed from its flowable to its remembered or elastic form on being cured. The composition also should not harm soft tissue structure in the mouth of the patient; be substantially non-toxic in use; and not induce allergic reactions of substance in the patient population as a whole. The composition should be easily removed from the soft tissue also and accurately record the soft tissue shape in the permanent elastomeric remembered form of the impression.

The present invention in a preferred embodiment of one of its aspects is the utilization of the new composition of the present invention for application to living mammalian tissue and curing the material in contact with the living mammalian tissue to set the impression thereof. The new composition in a preferred aspect of the present invention in a preferred embodiment is the most preferred use in a method of forming a dental impression in the oral cavity. A composition that is flowable, at least substantially free of memory and capable of assuming a permanent elastomeric memory in response to contact by actinic light, is engaged with the surfaces that are to have their dental impression made. This includes, in a preferred embodiment, forcing a tray of the composition toward the surface until some of the composition flows to assure a good engagement of the composition with the surfaces to be recorded. The tray is preferably maintained in contact with the composition to hold it securely in place and actinic light is passed through at least an integral part of the tray activating the photopolymerizing of the composition to a degree where the composition assumes a permanent elastic-remembered form. It has been found that the impression can be made on a wet surface, i.e. the mouth fluids do not have to be cleaned, without detrimental affect.

A preferred tray passes actinic light through all of its mass to the composition. For this purpose the tray may be a clear plastic.

In its preferred form, the method includes aspects of the materials that can perform the needed actions for preferred performance of the preferred methods of the present invention. The preferred method does not require pre-mixing of the composition before it is used. The compositions are preferably flowable, deformable and substantially free of any shape memory prior to activation by actinic light so that the composition can be formed to the dental impression including the adjacent soft tissue surfaces of the oral cavity. The preferred composition assumes a permanent elastomeric-remembered form in response to actinic light exposure. By permanent elastomeric-remembered form it is meant that the dental impression material can be stripped from the teeth by stretching and deforming in response to pressure applied by, in the usual usage the human hand, to pull the material off the teeth while retaining the remembered shape of the teeth in detail.

The one-component composition of the present invention can be packaged in various ways including being preloaded into a syringe, from which the dentist can express the material directly onto the soft or hard tissues to be reproduced. The composition can also be preloaded into a dental impression tray which can be placed by the dentist directly into the mouth of the patient or can be preloaded into a collapsible tube from which the dentist can squeeze the material into a dental impression tray which passes actinic light prior to placement in the patient's mouth. An important point is that the container or its overwrap be metal or otherwise opaque to actinic light or be packaged in such a manner as to protect the composition of the invention from actinic light prior to use by the dentist.

In a preferred embodiment of the present invention, the dentist places the special tray filled with the composition of the present invention in the mouth of the patient in such a way that the impression material fully contacts the entire area of the oral tissues of which an impression is being made. An optional step may be taken by the dentist prior to placing the filled tray in the patient's mouth in order to avoid entrapping air bubbles at the tissue surface, whereby the dentist would coat the surface of the tissues, especially constricted areas such as between teeth, with a more fluid impression material of the present invention, preferably by extrusion from a syringe, after which the bulk of the impression material; confined within an impression tray is then placed against the tissues.

After placement of the special tray, polymerization of the impression material is initiated with actinic light and polymerized preferably within 5 minutes, more preferably within 2 minutes and most preferably within 1 minute or less. The actinic light is preferably visible light from a source such as the PRISMETICS ® lite polymerization units of The L. D. Caulk Company, which produces visible light with a band of wavelengths between 400 and 500 nanometers and an energy output of approximately 550 milliwatts per square centimeter from the tip of the unit's light guide. The polymerization time can vary depending on the intensity and wavelength of the light used, the quantity of material to be polymerized and the tray used. For example, the tray could be a special tray of the construction described below.

The time required for the dentist and the patient to wait for polymerization or setting of the shape to take place may be reduced from 8-10 minutes down to two minutes or less, and the total time required for placement and curing of the one-component impression material of the present invention may be reduced to 2-3 minutes, as compared to approximately 15 minutes in conventional techniques which require mixing of two-component impression materials.

The impression tray to be used with the composition of the present invention must be capable of transmitting light to all areas of the impression material that are to be activated directly by the actinic light. One simple construction would be simply a standard transparent plastic tray whereby polymerizing light can be directed through all portions of the base of the tray onto the material inside the tray.

A suitable tray is the subject of U.S. Pat. No. 4,553,936; other suitable trays are the subject of U.S. patent application Ser. No. 032,903 to Hare et al, filed Mar. 31, 1987, now U.S. Pat. No. 4,867,680 and U.S. patent application Ser. No. 120,304, filed Nov. 13, 1987, now U.S. Pat. No. 4,867,682 which are assigned to the same assignee as the present patent application. This tray has a light-guide means such as a short solid light pipe rod at the anterior portion of a transparent tray which transmits light from the light source to the tray. The light is then transmitted to the impression material by the body of the tray itself. The light may be reflected or deflected directly into the material by a reflective tray surface. Such reflective surfaces are provided by metallized mirror-like coatings on the outer tray surface, or by geometric shaped facets, grooves or ridges which reflect or deflect light at roughly 90° from the general surface of the tray. The facets, grooves or ridges occur either on the outer or inner tray surfaces.

A special impression tray could be prefilled with impression material and be wrapped entirely with a metal foil-plastic laminate material to be opened at an area allowing for the taking of the impression only at the time of use, which would prevent the impression material from being exposed to light before use. The metal foil could serve the dual function of preventing unintentional light exposure and subsequently providing a reflecting surface for the light supplied to the tray to bring about polymerization.

The impression material of the invention has been found to be suitable for adding on. For example, if the impression material is not completely cured, or if an insufficient quantity of material has been dispensed on the tray, a partial impression or incompletely cured impression may be removed from the mouth, light body impression material may be added to the tray and/or the teeth, and the impression can then be completed. The bond between the impression material in the tray and the impression material added on is homogeneous and complete.

The preferred materials of the present invention have special applications in dentistry in addition to their most preferred application in preparing dental impressions. By dental impressions it is meant, reverse images of dental features in the mouth to serve as molds from which dental prosthesis can be prepared or models for preparing dental prosthesis can be prepared. The preferred materials of the present invention also have application in methods of directly preparing dental prosthesis by which term it is meant to include parts of dental prosthesis. This provides the format for an entirely new method of preparing dental prosthesis. A particularly preferred aspect of the present invention is the preparing of dental prosthesis by relining of dentures that are either damaged or no longer fit properly and/or comfortably.

The material is relatively soft and plastic so that it conforms with the contours of the gums, but is relatively substantial and durable so that it stays in place, retains its shape, and stays soft and pliable and does not break-up when the stresses of mastication are encountered.

The dentist would take a removable denture which is no longer fitting comfortably in a patient's mouth and apply to all of the areas of the denture which contact the patient's soft tissue, a thin coating of one of the compositions of the present invention. The dentist would then insert the denture into the patient's mouth and engage the composition while it is flowable and at least substantially free of memory with the surfaces in the oral cavity that are to be reproduced as the new closely fitting negative dental prosthetic part of the surface. The denture is pushed firmly into place, forcing the composition against the patient's dental surface until some of the composition flows into good conformity with the surface to form the composition into an accurate negative impression of the oral surface. The denture may then be cured by irradiation with actinic light through the ill fitting denture, and/or it may be removed from the patient's mouth and polymerized with actinic light. Preferred actinic light-cured apparatus of the present invention may include the PRISMETICS ® lite and/or a TRIAD ® light curing unit.

A very effective procedure would be to insert the denture into a TRIAD ® light-curing unit (a product of Dentsply International Inc.) wherein actinic light would be impinged on the negative impression formed composition by operation of the unit to photopolymerize the composition to a degree that the composition assumes a permanent elastomeric remembered form of the negative of the oral surface.

It will be understood that the flowable composition is carried on the surface of the removable denture that is to be juxtaposed against the soft tissue in the oral cavity when said composition is forced toward the soft tissue surface. The actinic light, except for ambient light, is preferably substantially limited to the visible light spectrum of about 360 to about 600 nanometers. If, on reinsertion, everything is not as desired, adjustment can be easily made by stripping off the reline prosthesis or cutting out a portion of it and repeating the forming process directly to the soft tissue as described.

The composition of the present invention in its actinic light-cured form is preferably substantially stable against assuming a permanent remembered form when stored actinic light free. The composition is preferably non-toxic in use in the oral cavity; stable in storage for at least one month as a one-component composition when actinic light free; and assumes a permanent elastomeric memory when exposed to light filtered to limited wavelengths within the visible light range for one minute to a depth of one inch.

It has been found that the polymer made according to the invention is suitable for use in a number of applications. For example, when using lower molecular weight materials, to provide for a rigid structure, the polymer of the invention can be used to make a personalized mouthguard (for sports) or nightguard (to prevent grinding of teeth). The mouthguard or nightguard can be made in much the same manner as a dental impression. That is, the polymer may be placed in the mouth to obtain an impression of the general features of the mouth, and the polymer can then be light cured in the mouth or removed from the mouth and cured.

It has been found that although the polymeric material is hydrophilic, it does not absorb excessive amounts of water and therefore can be used in the mouth for an extended period of time when used as, for example, a soft denture liner or mouthguard.

As will be apparent to those skilled in the art, the polymer of the invention can also be used to stabilize dental equipment in the mouth; as a tissue conditioner and medicament carrier used to treat the soft tissue in the mouth; as a rubber dam clamp sealer; a hemastatic retractor; impression material for removable prosthodontics; material to secure matrix bands and wedges in restorative procedures; medical wound dressing material; as a substitute for epoxy molds; as a pipe sealer (for example, for PVC); as an oral dressing over implants after re-entry to place post and cores; as a protective covering over ortho brackets to prevent or minimize trauma; as translucent, intraoral or direct, stint for pontics or temporaries; for making impressions for hearing aids; and for prosthetics, especially for facial use.

Other uses inside and outside dentistry will be readily apparent to those skilled in the art.

The impression material may be loaded immediately prior to use or in the factory with substances or medicaments that can be used to treat or reduce pain in the gums. For example anti-inflammatory agents, anti-bacterial agents or astringents such as aluminum chloride or epinephrine, and others may be used as needed.

The invention is further illustrated by the following examples:

EXAMPLE 1

A preferred isosyanatoethyl methacrylate urethane methacrylate oligomer elastomeric prepolymer compound was prepared according to the following formulation:

| | |
|---|---|
| Polypropylene glycol MW-2,000 Voranol 2120 (Dow Chemical) | 690 g |
| Trimethyl hexamethylene diisocyanate (Thorson) | 145 g |
| Dibutyl tin dilaureate | 0.4170 g |
| Hydroxyethylmethacrylate (HEMA) (Esschem) | 50.0 g |
| 1,4 Butane diol (BASF) | 31.0 g |
| Isocyanatoethyl methacrylate (Dow Chemical) | 53.4 g |

The procedure was as follows:

One mole of polypropylene glycol (2 equivalents of hydroxy) are reacted with two moles of trimethyl hexamethylene diisocyanate (4 equivalents of isocyanate) employing the dibutyl tin dilaureate.

The polypropylene glycol was dewatered with molecular sieve (4A) for two days. Then it was charged into a 2 liter reactor. Stirring and dry air flow through the reactor was begun. The dibutyl tin dilaureate was added to the glycol dropwise and allowed to stir in. Then the trimethyl hexamethylene diisocyanate was added to the glycol-catalyst mixture dropwise using a separatory funnel. The addition was done at room temperature and The drop rate was controlled to keep the temperature below 50° C. After about three hours, all the diisocyanate had been added. The mixture was allowed to stir overnight with a heating mantle up around the reactor (no heat turned on). The next day 45 grams HEMA was added dropwise, again controlling the drop rate to keep the pot temperature below 50° C. After all the HEMA was added, the 1,4 Butane diol was added dropwise to the reactor contents. This mixture was allowed to stir overnight. The next day, isocyanatoethyl methacrylate was added dropwise through the separatory funnel and stirred in. A slight excess of HEMA (5 grams) was finally added to the pot about three hours after the final addition of isocyanatoethyl methacrylate to be sure all the free isocyanate was reacted. The pot contents were allowed to stir for 24 hours and then unloaded.

EXAMPLE 2

A dental impression forming composition was compounded by hand mixing the following formulation at ambient conditions.

| | |
|---|---|
| Resin of EXAMPLE 1 | 100 parts by wt. |
| Camphoroquinone | 0.15 parts by wt. |
| Methyl diethanol amine (MDEA) | 0.5 parts by wt. |

The dental impression forming composition was then tested for its relevant characteristics with the following results:

The composition was irradiated with a 500 watt General Electric Photo-EBV photoflood lamp containing light from the visible light spectrum for 5 minutes with the lamp approximately 2 inches from the dental impression forming composition specimen. The material cured to an elastic solid. The following testing results were obtained using ADA Spec 19 (1984) for non-aqueous elastomeric impression materials when the cured dental impression composition cured by irradiation as described was tested:

| Compression Set (%) | Strain (%) | Dimensional Change (%) |
|---|---|---|
| 0.65 | 3.75 | 24 hrs 0.23 expansion |
| | | 1 wk 0.27 expansion |

EXAMPLE 3

A dental impression forming composition was compounded by hand mixing the following two formulations separately at ambient conditions.

The catalyst paste was prepared according to the following formulation:

| | |
|---|---|
| 1. resin | 52.05 parts by wt. |
| 2. benzoyl peroxide | 1.04 parts by wt. |
| 3. filler | 27.33 parts by wt. |
| 4. polypropylene glycol (MW 4,000) | 19.52 parts by wt. |
| 5. BHT (butylated | 0.06 parts by wt. |

-continued

| | |
|---|---|
| hydroxy toluene) | |

A base paste was prepared according to the following formulation:

| | |
|---|---|
| 1. resin | 51.80 parts by wt. |
| 2. dihydroxy ethyl p-toluidine | 0.93 parts by wt. |
| 3. filler | 27.20 parts by wt. |
| 4. polypropylene glycol (MW 4,000) | 19.43 parts by wt. |

The two pastes were mixed at an equal weight ratio by spatulating on a parchment pad for approximately 45 seconds. The material cured to an elastic solid with a shore A hardness of about 55 (ASTM 19, 1984 testing method) in 6 minutes at ambient temperature.

Below are the results of testing this material in accordance with ADA Spec 19 referred to in Example 2:

| Dimensional Change % | Mix (mm) Consistency | Compression Set (%) | Strain (%) | Flow (%) |
|---|---|---|---|---|
| 24 hrs. 0.17 | 49 | 0.5–0.6 | 2.5–3.5 | 0.10 |
| 1 wk. 0.18 | | | | |

The material was determined to be compatible with gypsum and detailed reproduction was fine when tested in accordance with ADA Specification 19 for non-aqueous elastomeric materials.

EXAMPLE-4

Another preferred isocyanatoethyl methacrylate urethane methacrylate oligomer elastomer prepolymer compound was prepared according to the following formulation

| | |
|---|---|
| Polypropylene glycol (MW 4000) Voranol 2140 (Dow Chemical) | 834.6 g |
| Trimethylhexamethylene diisocyanate (Thorson Chemicals) | 87.7 g |
| Stannous octoate | 0.50 g |
| Hydroxyethyl methacrylate (Rohm & Haus) | 27.1 g |
| 1,4 Butanediol (BASF) | 18.7 g |
| Isocyanatoethyl methacrylate | 30.8 g |

The procedure was as follows:

In theory, one mole of polypropylene glycol (2 equivalents of hydroxy) are reacted with two moles of trimethylhexamethylene diisocyanate (4 equivalents of isocyanate) employing the stannous octoate as catalyst.

The polypropylene glycol was charged into a 2 liter reactor. Stirring and dry air flow through the reactor was begun. The stannous octoate was charged to the reactor and allowed to stir in. Then the trimethylhexamethylene diisocyanate was added to the glycol catalyst mixture dropwise using a separatory funnel. The addition was done at room temperature and was controlled to keep the temperature below 50° C. Addition was complete after 30 minutes. The contents were allowed to stir for 30 minutes more. Samples were taken and titration was done to determine isocyanate content. Isocyanate was found to be 1.9% which indicated complete reaction of the polypropylene glycol and trimethyhexamethylene diisocyanate. Then the 27.1 grams of HEMA were added all at once to the reactor contents which were at a temperature of about 40° C. The contents were allowed to stir for 45 minutes. Then titration samples were taken and the isocyanate content determined to be 0.95%. This indicated complete reaction of the HEMA with the isocyanate terminated prepolymer leaving 1 equivalent of isocyanate sites for reaction with 1,4 butane diol. At this point 18.7 grams of 1,4 butane diol were added to reactor contents all at once and allowed to stir in for 2 hours. The temperature of the reactor continued between 40 and 50° C. for this procedure. At the end of 2 hours the isocyanatoethyl methacrylate was added dropwise to the reactor using a separatory funnel. This addition took approximately 30 minutes. Stirring was continuous until the next morning to be sure all the free isocyanate was reacted. Then the pot contents were unloaded.

EXAMPLE-5

A dental impression forming composition was compounded by hand mixing the following formulation at ambient conditions.

| | |
|---|---|
| Resin of EXAMPLE 4 | 12.27 g |
| Camphorquinone | 0.031 g |
| 4-Ethyldimethylaminobenzoate | 0.200 g |
| Butylated hydroxy toluene | 0.025 g |
| Crystobalite filler | 9.83 g |
| fumed silica (Aerosil R-972 from Degussa) | 1.75 g |
| blue pigment (Dayglo) | 0.035 g |
| Alkyl benzyl phthalate | 0.88 g |

The composition was irradiated for 2 minutes with a 500 watt GE Photoflood lamp containing light from the visible light spectrum with the lamp approximately 2 inches from the dental impression forming composition specimen. The material cured to an elastic solid.

EXAMPLE-6

A dental impression forming composition was compounded by hand mixing the following formulation at ambient conditions:

| | |
|---|---|
| Resin of EXAMPLE 4 | 39.0 g |
| Di ($C_{7-9-11}$ Alkyl) Phthalate (Palatinol 711 P from BASF) | 1.60 g |
| Peppermint Oil | 0.20 g |
| Titanium IV neoalkoxy, tris (dodecylbenzene) sulfanato (Ken React LICA 09 from Kenrich Petrochemicals, Inc.) | 0.20 g |
| fumed silica (Aerosil R-972 from Degussa) | 4.20 g |
| blue pigment (Dayglo) | 0.080 g |
| Feldspar | 35.5 g |
| Camphorquinone | 0.10 g |
| 4 Dimethylaminobenzonitrile | 0.24 g |

The composition was irradiated for 1 minute using the photoflood lamp procedure of Example 2. The material cured to a elastic solid.

The depth of cure was tested using the Presmetics ® light earlier described. A sample of material 20 mm thick was covered with a sheet of clear Mylar about 1 mil thick. The sheet was in direct contact with the sample. The light was directly engaged against the sheet of Mylar. The light was on 10 seconds. Curing was to a depth of 8 mm as determined by wiping away the uncured material from the bottom of the sample and measuring the remaining cured material.

EXAMPLE-7

A dental impression forming compound of the following formulation was compounded by a double planetary mixer at reduced pressure:

| Resin of EXAMPLE 4 | 45.98 g |
|---|---|
| Camphorquinone | 0.09 g |
| 4-Dimethylaminobenzonitrile | 0.4 g |
| Butylated Hydroxy Toluene | 0.05 g |
| Di ($C_{7-9-11}$ Alkyl) Phthalate (Palatinol 711 P from BASF) | 2.0 g |
| Titanium IV neoalkoxy, tris (dodecylbenzene) sulfanato (as in Example 6) | 0.25 g |
| Fused Quartz | 43.6 g |
| fumed silica (as in Example 6) | 7.6 g |
| green pigment (Dayglo) | 0.10 g |
| blue pigment (Dayglo) | 0.02 g |

The composition was irradiated for 40 seconds using the photoflood lamp procedure of Example 2. The material cured to a rubbery solid.

The depth of cure test procedure of Example 6 was preformed and the depth of cure was 13 to 14 mm. The material gave the following physical properties as tested by ADA Spec. #19 referred to in Example 2:

| Compression Set | Strain | Dimensional Change | Detail Reproduction | Flow |
|---|---|---|---|---|
| 1% | 2.6% | 0.05% | 20 micron line | 0.10% |

EXAMPLE-8

The procedure of Example 7 was repeated except the formula was as follows:

| Resin of EXAMPLE 4 | 39.64 g |
|---|---|
| Camphorquinone | 0.08 g |
| 4-Ethyldimethylaminobenzoate | 0.24 g |
| Butylated hydroxy toluene | 0.04 g |
| Di ($C_{7-9-11}$ Alkyl) Phthalate (as in | 2.0 g |
| Titanium IV neoalkoxy, tris (dodecylbenzene) sulfonato (as in EXAMPLE 6) | 0.25 g |
| Fused Quartz | 43.74 g |
| fumed silica (as in EXAMPLE 6) | 14.0 g |
| blue pigment (Dayglo) | 0.07 g |

The composition was irradiated using the procedure of Example 7. The material cured to a stiff, but rubbery solid and gave the following physical properties as tested by ADA Spec #19 referred to in Example 2:

| Compression Set | Strain | Dimensional Change | Detail Reproduction | Flow |
|---|---|---|---|---|
| 0.85% | 1.8% | N/A | 20 micron line | N/A |

EXAMPLE-9

A dental impression forming compound of the following formulation was compounded by a double planetary mixer at reduced pressure:

| Resin of EXAMPLE 4 | 390.41 g |
|---|---|
| Camphorquinone | 0.79 g |
| Butylated Hydroxy Toluene | 0.170 g |
| 4-Dimethylaminobenzonitris | 3.63 g |
| Fused Quartz of EXAMPLE 7 | 437.3 g |
| Magenta Pigment (Dayglo) | 0.80 g |
| fumed silica (as in EXAMPLE 6) | 139.9 g |
| gamma-Methacryloxypropyltrimethoxysilane | 5.00 g |
| Di ($C_{7-9-11}$ Alkyl) Phthalate (as in EXAMPLE 6) | 19.50 g |
| Titanium IV neoalkoxy, tris (dodecylbenzene) sulfonato (as in EXAMPLE 6) | 2.50 g |

The composition was tested for depth of cure using the procedure of example 6 and gave results of 19-20 mm. The composition was irradiated for 40 seconds with a Prismetics lite using the wide tip with the tip directly above the dental impression forming composition specimen using a Mylar spacer. The material cured to a rubbery solid and gave the following physical properties as tested by ADA Spec. #19 referred to in Example 2:

| Impression Set | Strain | Dimensional Change | Detail Reproduction |
|---|---|---|---|
| 0.60% | 1.1% | 0.02% | 20 micron line |

EXAMPLE 10

A syringeable viscosity dental impression forming compound of the following formulation was compounded in a double planetary mixer at reduced pressures:

| Resin of EXAMPLE 4 | 456.1 g |
|---|---|
| Camphorquinone | 0.92 g |
| Butylated Hydroxy Toluene | 0.20 g |
| 4-Dimethylaminobenzonitrile | 2.81 g |
| Blue pigment (Dayglo) | 2.514 g |
| Fused Quartz of EXAMPLE 7 | 434.6 g |
| fumed silica (as in EXAMPLE 6) | 75.9 g |
| Di ($C_{7-9-11}$ Alkyl) Phthalate (as in | 19.5 g |
| Titanium IV neoalkoxy, tris (dodecylbenzene) sulfonato (as in EXAMPLE 6) | 2.50 g |
| gamma-Methacryloxypropyltrimethoxysilane | 5.00 g |

The composition was tested for depth of cure using the procedure of example 6 and gave results of 15 to 16 mm. The composition was irradiated for 40 seconds with a Prismetics lite using the wide tip with the tip directly above the dental impression forming composition specimen using a Mylar spacer. The material cured to a rubbery solid and gave the following physical properties as tested by ADA Spec. #19 referred to in Example 2:

| Compression Set | Strain | Detail Reproduction | Dimensional Change |
|---|---|---|---|
| 0.72% | 1.9% | 20 micron line | 0.04% |

Example 11

| Voranol 2120 (polypropylene glycol) (MW 2000) | 68.25% |
|---|---|
| TMDI (Trimethylhexamethylene diisocyanate) | 14.34% |
| Stannous Octoate | 0.05% |
| HEMA (Hydroxyethyl methacrylate) | 3.14% |
| 1,4 - Butanediol | 4.29% |

| | |
|---|---|
| TIM (Reaction product of TMDI and HEMA) | 8.10% |
| HEMA | 1.82% |
| Phosphoric Acid - Water Solution (1:1) | 0.0021% |

The polypropylene glycol (Voranol 2120) with an average molecular weight of 2000 is first mixed with the phosphoric acid solution. This neutralizes residual base in the polypropylene glycol which can act as a catalyst in the prepolymer reaction with TMDI. Then the stannous octoate is added as the catalyst for urethane formation. A 2/1 excess of TMDI is added to form an isocyanate terminated prepolymer. Then part of the residual isocyanate is capped with HEMA. The remainder is chain extended with 1,4-Butanediol. Then TIM is added. TIM is the reaction product of 1 mole (2 equivalents) of TMDI and 1 mole (1 equivalent) of HEMA. It has one free isocyanate end and one methacrylate end when the reaction is complete. The isocyanate portion reacts with the remaining hydroxyl group from 1,4-Butanediol. Finally, a small amount of HEMA is added to react any residual isocyanate.

A comparison of moles and equivalents of the ingredients is seen below:

| | Moles | Equivalents |
|---|---|---|
| Voranol 2120 | 1 | 2 |
| TMDI | 2 | 4 |
| HEMA | 0.7 | 0.7 |
| 1,4-Butanediol | 1.4 | 2.8 |
| TIM | 0.7 | 0.7 |
| HEMA | 0.4 | 0.4 |

| Activated Resin | |
|---|---|
| Resin described above | 98.78% |
| Camphorquinone | 0.20% |
| 4-Dimethylaminobenzonitrile | 0.92% |
| Butylated Hydroxy Toluene (BHT) | 0.10% |
| Heavy Body Tray Material | |
| Activated Resin described above | 45.95% |
| Fused Quartz (average particle size 15-25 microns) | 42.37% |
| Aerosil R-972 fumed silica | 9.04% |
| Dayglo A-21 Corona Magenta pigment | 0.0824% |
| Palatinol 711P (Di-C7-9-11) Alkyl Phthalate | 2.00% |
| Ken React LICA 09 | 0.05% |
| Gamma-Methacryloxypropyltrimethoxysilane | 0.50% |
| Light Body Syringeable Material | |
| Activated resin described previously | 54.76% |
| Fused Quartz (average particle size 15-25 microns) | 39.68% |
| Aerosil R-972 fumed silica | 1.55% |
| Dayglo A-19 Horizon Blue pigment | 0.25% |
| Palatinol 711P (Di-C7-9-11) Alkyl Phthalate | 3.10% |
| Ken React LICA 09 | 0.13% |
| Gamma-Methacryloxypropyltrimethoxysilane | 0.52% |

The attached table provides a comparison of the properties of the material of this example as compared with ADA specs.

The material with either resin has the advantages of unlimited work time, no mixing, command cure, and a fast cure. Furthermore, the impression has good readability, is hydrophilic, and can be poured up immediately in gypsum or epoxy.

In a preferred embodiment, peppermint may be added to the heavy body material.

| | Material of Example 11 | | |
|---|---|---|---|
| Properties | Heavy Body Tray Material | Light Body Syringeable Material | ADA Spec. 19 |
| Work Time | Unlimited in black storage. In ambient light material is workable for 4' to 5' | Unlimited in black storage. In ambient light material is workable for 4' to 5' | Minimum 2'00" |
| Set Time | Immediately after light cure | Immediately after light cure | Maximum 10'00" |
| Depth of Cure (mm) | 20 | 20 | — |
| Compression Set (%) | 1.4 | 1.1 | Maximum 2.5 |
| Strain (%) | 2.1 | 5.4 | 2.0-20.0 |
| Dimensional Change (%) | 0.25 | 0.20 | Maximum 0.5 |
| Detail Reproduction | 20 micron line | 20 micron line | 20 micron line |
| Compatibility Gypsum | Yes | Yes | Yes |
| Copper Metalizing Bath | Yes | Yes | Yes |
| Silver Metalizing Bath | Yes | Yes | Yes |

EXAMPLE 12

The resin of example 11 was compounded into heavy body and light body impression pastes under reduced pressures according to the formulas below:

| Heavy Body Tray Material | |
|---|---|
| Resin of EXAMPLE 11 | 45.31% |
| Camphorquinone | 0.092% |
| 4-Dimethylaminobenzonitrile | 0.422% |
| Butylated Hydroxy Toluene | 0.0459% |
| Ground Fused Quartz (average particle size 15-25 microns) | 43.72% |
| Aerosil R-972 fumed silica | 7.50% |
| Dayglo Corona Magenta colorant | 0.082% |
| Palatinol 711P (Di C7-9-11 Alkyl Phthalate) | 2.00% |
| Peppermint Oil | 0.20% |
| Ken React LICA 09 | 0.10% |
| gamma - Methacryloxypropyltrimethoxysilane | 0.50% |
| Light Body Syringeable Material | |
| Resin of EXAMPLE 11 | 55.23% |
| Camphorquinone | 0.11% |
| 4-Dimethylaminobenzonitrile | 0.51% |
| Butylated Hydroxy Toluene | 0.11% |
| Ground Fused Quartz (average particle size 15-25 microns) | 37.63% |
| Aerosil R-972 fumed silica | 2.42% |
| Dayglo Horizon Blue colorant | 0.25% |
| Palatinol 711P (Di C7-9-11 Alkyl Phthalate) | 3.10% |
| Ken React LICA 09 | 0.13% |
| gamma - Methacryloxypropyltrimethoxysilane | 0.50% |

EXAMPLE 13

An isocyanatoethyl methacrylate urethane methacrylate oligomer elastomer prepolymer compound was prepared according to the formulation and procedure of EXAMPLE 4. This resin was then compounded according to the formula below under reduced pressure:

| | |
|---|---|
| Resin of EXAMPLE 4 | 46.05% |
| Camphorquinone | 0.093% |
| 4-Dimethylaminobenzonitrile | 0.279% |
| Butylated Hydroxy Toluene | 0.046 |
| Silanated Fused Quartz | 43.54% |
| Fumed Silica (Aerosil R-972) | 7.563% |
| Dayglo blue pigment | 0.067% |
| Di($C_{7-9-11}$ Alkyl) Phthalate (Palatinol 711P from BASF) | 1.96% |
| Peppermint Oil | 0.15% |
| Titanium IV neoalkoxy, tris (dodecylbenzene) sulfonato (as in EXAMPLE 6) | 0.25% |

Three Dimensional change specimens of the above material were made in the recommended ADA Spec 19 mold by filling and curing 1 minute under the photoflood lamp of EXAMPLE 2. After curing the specimens were demolded and readings of the length of the lines were taken according to ADA Spec. 19. After this immediate reading the specimens were each immersed in 250 ml of deionized water and stored at 37° C. Periodically, the specimens were removed and readings of the ruled line length were taken and recorded The percentage of change was calculated and is shown in the table below illustrating the dimensional stability of the material with time in a wet environment:

| Average % Dimensional Change 1 week | Average % Dimensional Change 1 month | Average % Dimensional Change 3 months | Average % Dimensional Change 16 months |
|---|---|---|---|
| +0.34% expansion from immediate reading | +0.31% expansion from immediate reading | +0.31% expansion from immediate reading | +0.19% expansion from immediate reading |

Furthermore, the material was noted to be soft and pliable throughout the period of 16 months in the water.

EXAMPLE 14

A non-staining VLX soft denture liner was prepared according to the following procedures:

A heavy paste 1 was made in a double planetary mixer under reduced pressure using the resin of Example 11 according to the formula below.

| | |
|---|---|
| Resin of EXAMPLE 11 | 45.36% |
| Camphorquinone | 0.092% |
| 4-Dimethylaminobenzonitrile | 0.422% |
| Butylated Hydroxy Toluene | 0.046% |
| Ground fused quartz (mean particle size 15-25 microns) | 42.37% |
| Fumed Silica (aerosil R-972) | 9.04% |
| Dayglo Corona Magenta | 0.082% |
| Palatinol 711P | 2.00% |
| gamma-Methacryloxypropyltrimethoxy silane | 0.50% |
| Ken React LICA 09 | 0.1% |

A paste 2 was made by hand using silicone methacrylate resin according to the formula below:

| | |
|---|---|
| Silicone Methacrylate Resin (P5X2294 from Petrarch Systems, Inc.) | 45.37% |
| 4-Dimethylaminobenzonitrile | 0.42% |
| Camphorquinone | 0.092% |
| Butylated Hydroxy Toluene | 0.023% |
| Ground Fused Quartz (mean particle size 15-25 microns) | 42.37% |
| Fumed silica (Aerosil R-972) | 9.04% |
| Dayglo Corona Magenta | 0.080% |
| Ken React LICA 09 | 0.10% |
| Palatinol 711P | 2.00% |
| gamma-Methacryloxypropyltrimethoxysilane | 0.50% |

Then, 25 parts of Paste 1 was mixed by hand with 25 parts of Paste 2 to give Paste 3. Discs of Pastes 1, 2, and 3 were made in 3 mm×20 mm stainless steel rings and cured under a Photoflood lamp for 30 seconds. Then these specimens were placed in coffee and tea for 24 hours at 37° C. After removal from the coffee and tea the discs were rinsed and blotted dry. The specimens were examined visually for staining. Paste 1 was severely stained. Paste 3 had slight to moderate staining. Paste 2 was the best with minor staining. Upon examination of the discs, it was found that Paste 3 appeared to have the best combination of reduced staining and elastomeric properties. Paste 2 was too rigid and brittle when cured to be a good soft denture liner.

EXAMPLE 15

Example 15 is an alternative method of preparing the new impression material resin of the invention.

| | |
|---|---|
| Voranol 2120 | 68.30% |
| Phosphoric Acid Water Solution (1:1) | 0.0021% |
| Stannous octoate | 0.049% |
| TMDI | 14.36% |
| HEMA | 3.15% |
| 1,4-Butanediol | 4.30% |
| TMDI | 5.02% |
| HEMA | 4.74% |
| Stannous octoate | 0.030% |
| BHT | 0.050% |

The Voranol 2120 was charged into a clean, dry 5 gallon water jacketed glass-lined reactor. The phosphoric acid-water solution was weighed out and charged into the reactor. The mixture was stirred for 2 hours under dry air flow through the reactor. The stirrer was stopped and the mixture was allowed to sit overnight under dry air flow. The next day the stannous octoate was weighed out, added to the reactor, and stirred 15 minutes. Then the first addition of TMDI was added to the reactor by a metering pump. Addition took 1½ hours. The mixture was stirred for another hour then the first addition of HEMA was added in 5 minutes and then stirred an additional 30 minutes. The temperature ranged from 33°-35° C. Then 1,4-Butanediol was added in 8 minutes and then stirred for an additional 1 hour. Next the second addition of TMDI was added over 45 minutes with the temperature ranging from 38°-44° C. The resin was stirred an additional hour. Then the second addition of stannous octoate was added and stirred 10 minutes. Finally, the second addition of HEMA was made in 5-10 minutes with the temperature ranging from 43°-44° C. Approximately 40 minutes later 48°-50° C. water was circulated through the jacket of the reactor. The temperature of the mixture was 52°-54°

C. and this temperature was maintained overnight by use of the heated circulation water. The next day a sample of the resin was taken and found to be free of residual diisocyanate. Then the BHT was added, the mixture was stirred for approximately one hour, and then discharged into a poly-lined drum.

While in accordance with the patent statutes, what is considered to be the preferred embodiment of the invention has been described, it will be obvious to those skilled in the art that numerous changes and modifications may be made therein without departing from the invention and it is therefore aimed in the appended claims to cover all such equivalent variations as fall within the true spirit and scope of the invention.

It is claimed:

1. An elastomeric composition for use in dentistry comprising a compound of the general formula:

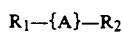

wherein
R₁ is

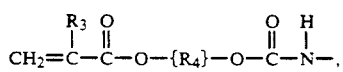

R₂ is

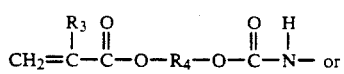

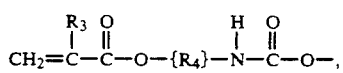

R₃ is H, alkyl of 2-10 carbons, substituted alkyl of 2-10 carbons, aryl of 6-14 carbon, substituted aryl of 6-14 carbons, F, or CN and R3 may be the same or different in each position;

R₄ is a divalent hydrocarbon radical or divalent substituted hydrocarbon radical and may be straight or branched chain or cyclic or a combination thereof from 2-10 carbons; and A is a polyurethane, polyether or polyester group; from 5 to 95 percent by weight fillers and a photoinitiator, wherein substituted represents a chemical substituant selected from the group consisting of halogen, lower alkyl having from 1 to 6 carbon atoms, oxy lower alkyl having from 1 to 6 carbon atoms, silyl lower alkyl having from 1 to 6 carbon atoms, phenyl, halophenyl, alkoxyphenyl, trihalomethyl and dihalomethyl having from 1 to 6 carbon atoms, and wherein said composition has a molecular weight of about 500-4000 and a viscosity suitable for use as an oral bandage or a dental impression material and is non-toxic in use in the oral cavity, stable in storage for at least one (1) month as a one-component composition when actinic light free, and assumes a permanent elastomeric memory suitable for use as an oral bandage or a dental impression material when exposed to light filtered to limited wavelengths substantially within the visible light range for one (1) minute to a depth of one (1) inch.

2. A new impression material for application to mammalian tissue and curing in contact therewith to set the impression thereof; said impression material comprising free radical initiated polymerizable resin present in an amount of about 5 to 95% by weight of the total composition; alkyl benzensulfonyl titanate present in an amount of about 0.001 to about 2% by weight of the total composition; a polymerization initiator present in an amount of about 0.001 to about 10% by weight of polymerizable resin; and filler present in an amount of about 5 to 95% by weight of the total composition.

3. The new impression material of claim 2 wherein said free radical initiated polymerizable resin is present in an amount of about 10 to 80% by weight of the total composition; said alkyl benzensulfonyl titanate is neopentyl (diallyl) oxy tri (dodecyl) benzenesulfonyl titanate and is present in an amount of about 0.005 to about 1% by weight of the total composition; said polymerization initiator is present in an amount of about 0.01 to about 5% by weight of polymerizable resin; and filler is present in an amount of about 20 to about 90% by weight of the total composition.

4. A soft denture liner comprising a compound of the general formula:

wherein
R₁ is

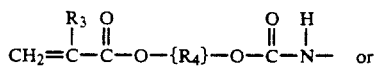

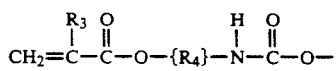

and each R₁ may be the same or different

R₃ is H, alkyl of 2-10 carbons, substituted alkyl of 2-10 carbons, aryl of 6-14 carbons, substituted aryl of 6-14 carbons, F or CN and R3 may be the same or different in each position R₄ is a divalent hydrocarbon radical or divalent substituted hydrocarbon radical and may be straight or branched chain or cyclic or a combination thereof having from 2-10 carbons and A is a polyurethane, polyether or polyester group, from 5 to 95 percent by weight fillers and a photoinitiator, wherein substituted represents a chemical substituent selected from the group consisting of halogen, lower alkyl having from 1 to 6 carbon atoms, oxy lower alkyl having from 1 to 6 carbon atoms, silyl lower alkyl having from 1 to 6 carbon atoms, phenyl, halophenyl, alkoxyphenyl, trihalomethyl and dihalomethyl and wherein said composition has a molecular weight of about 500-4000 and a viscosity suitable for use as a soft denture liner and is non-toxic in use in the oral cavity, stable in storage for at least one (1) month as a one-component composition when actinic light free, and assumes a permanent elastomeric memory suitable for use as a soft denture liner when exposed to light filtered to limited wavelengths substantially within the visible light range for one (1) minute to a depth of one (1) inch.

5. The soft denture liner of claim 4 in which [A] is

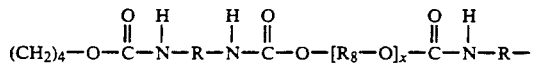

where R is alkyl of 2 to 25 carbons, $R_8$ is alkyl of 2 to 25 carbons, and x is 10 to 100.

6. The soft denture liner of claim 5 in which the new composition of matter of claim 1 wherein said compounds provides that general formula A is $[R_5]—X—[R_6]$ $R_5$ and $R_6$ are each divalent hydrocarbon radicals or divalent sub hydrocarbon radicals, X is a polyurethane, polyether, or polyester and $R_5$—X and $R_6$—X are joined by a urethane linkage and $R_5$ and $R_6$ have from 2 to 100 carbons.

7. The soft denture liner of claim 6 comprising a compound of the general formula

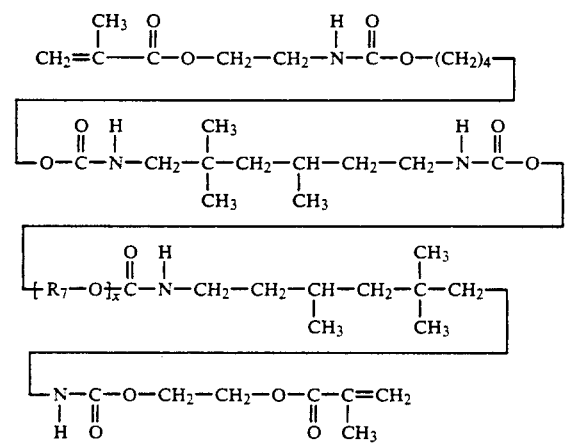

where $R_7$=alkylene, substituted alkylene or

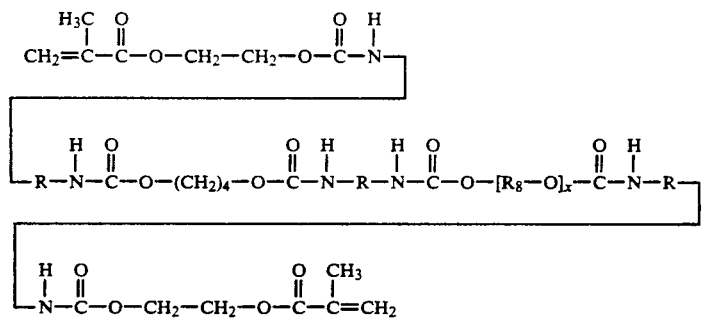

where,
$R_8$ is alkylene of 2 to 8 carbons,
R is alkyl of 2 to 25 carbons, and
x=10 to 100.

8. An elastomeric composition for use in dentistry comprising a compound of the general formula:

$R_1$—{A}—$R_2$ wherein
$R_1$ is

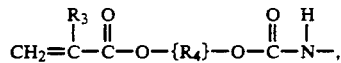

$R_2$ is

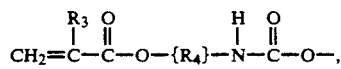

$R_3$ is H, alkyl of 2-10 carbons, substituted alkyl of 2-10 carbons, aryl of 6-14 carbons, substituted aryl of 6-14 carbons, F, or CN and $R_3$ may be the same or different in each position;

$R_4$ is a divalent hydrocarbon radical or divalent substituted hydrocarbon radical and may be straight or branched chain or cyclic or a combination thereof from 2-10 carbons; and A is a polyurethane, polyether or polyester group;
a photoinitiator and filler,
wherein substituted represents a chemical substituant selected from the group consisting of halogen, lower alkyl having from 1 to 6 carbon atoms, oxy lower alkyl having from 1 to 6 carbon atoms, silyl lower alkyl having from 1 to 6 carbon atoms, phenyl, halophenyl, alkoxyphenyl, trihalomethyl and dihalomethyl.

9. A soft denture liner composition comprising a compound of the general formula:

$R_1$—{A}—$R_1$ wherein
$R_1$ is

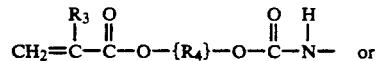 or

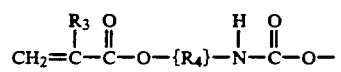

and each $R_1$ may be the same or different
$R_3$ is H, alkyl of 2-10 carbons, substituted alkyl of 2-10 carbons, aryl of 6-14 carbons, substituted aryl of 6-14 carbons, F or CN and $R_3$ may be the same or different in each position $R_4$ is a divalent hydrocarbon radical or divalent substituted hydrocarbon radical and may be straight or branched chain or cyclic or a combination thereof having from 2-10 carbons and

A is a polyurethane, polyether or polyester group
a photoinitiator and filler,
wherein substituted represents a chemical substituent selected from the group consisting of halogen, lower alkyl and having 1 to 6 carbon atoms, oxy lower alkyl and having 1 to 6 carbon atoms, silyl lower alkyl and having 1 to 6 carbon atoms, phenyl, halophenyl, alkoxyphenyl, trihalomethyl, and dihalomethyl.

10. The composition of claim 8 or 9 wherein said filler comprises 5 to 95 percent by weight of said composition.

11. The composition of claim 8 or 9 wherein said filler comprises fused quartz or silica.

12. The composition of claim 8 wherein said composition has a molecular weight of about 500-4000 and a viscosity suitable for use as an oral bandage or a dental impression material and is non-toxic in use in the oral cavity, stable in storage for at least one (1) month as a one-component composition when actinic light free, by exposing said composition to light filtered to limited wavelengths substantially within the visible light range to form an oral bandage, a dental impression.

13. The composition of claim 9 wherein said composition has a molecular weight of about 500-4000 and a viscosity suitable for use as a soft denture liner and is non-toxic in use in the oral cavity, stable in storage for at least one (1) month as a one-component composition when actinic light free, by exposing said composition to light filtered to limited wavelengths substantially within the visible light range to form a soft denture liner.

14. The composition of claim 1, 4, 8 or 9 further comprising a medicament.

15. The composition of claim 1, 4, 8 or 9 further comprising an accelerator.

16. The composition of claim 1, 4, 8 or 9 further comprising a titanate accelerator.

17. The composition of claim 8 or 9, wherein said filler has an organosilyl coating.

18. The composition of claim 1, 4, 8 or 9, wherein said composition has at least one tooth shape.

19. The composition of claim 1, 4, 8 or 9, wherein said filler comprises from 20 to 90 percent by weight of said composition.

20. The composition of claim 1, 4, 8 or 9, wherein said filler comprises from 40 to 85 percent by weight of said composition.

21. The composition of claim 1, 4, 8 or 9 further comprising plasticizer and catalyst.

22. The composition of claim 1, 4, 8 or 9 further comprising reducing agent.

* * * * *